United States Patent [19]

Engvall et al.

[11] Patent Number: 5,444,158
[45] Date of Patent: Aug. 22, 1995

[54] MEROSIN, NUCLEIC ACIDS ENCODING, FRAGMENTS AND USES THEREOF

[75] Inventors: Eva Engvall, Escondido, Calif.; Joshua Sanes, St. Louis, Mo.

[73] Assignees: La Jolla Cancer Research Foundation, La Jolla, Calif.; Washington University, St. Louis, Mo.

[21] Appl. No.: 87,642

[22] Filed: Jul. 8, 1993

Related U.S. Application Data

[63] Continuation of Ser. No. 587,689, Sep. 24, 1990, abandoned, which is a continuation-in-part of Ser. No. 472,319, Jan. 30, 1990, abandoned.

[51] Int. Cl.$^6$ ............... A61K 38/14; A61K 38/16; C07K 14/78
[52] U.S. Cl. ............... 530/395; 530/413; 530/417
[58] Field of Search ............... 530/395, 417, 413

[56] References Cited

PUBLICATIONS

Deutzmann et al, Eur. J. Biochem. 177 (1988), pp. 34–45.
Leivo, I. et al "Merosin, a protein specific for basement membranes of Schwann cells in development", Proc. Natl Acad Sci USA, 85:1544–48 (1988).
Engvall et al, "Merosin promotes cell attachment in RN22 Schwann cells," E. Cell Res., 198:115–123 (1992).
Ohno et al., Isolation of Laminin from Human Placental Basement Membranes: Amnion, Chorion and Chorionic Microvessels, Biochem. and Biophys. Res. Comm. 112:1091–1098 (1983).
George R. Martin and Rupert Timpl, Laminin and Other Basement Membrane Components, Ann. Rev. Cell Biol. 3:57–85 (1987).
Dale E. Hunter et al., A laminin–like adhesive protein concentrated in the synaptic cleft of the neuromuscular junction, Nature 338:229–233 (1989).
Arthur D. Lander et al., Laminin is associated with the "neurite outgrowth-promoting factors" found in conditioned media, Proc. Natl. Acad. Sci. USA 82:2183–2187 (1985).
George E. Davis et al., Isolation and Characterization of Rat Schwannoma Neurite-promoting Factor: Evidence that the Factor Contains Laminin[1], The Journal of Neuroscience 5:2662–2671 (1985).
J. G. Steele and H. Hoffman, Neurite-Promoting Activity From Fetal Skeletal Muscle: Partial Purification of a High-Molecular-Weight Form, Journal of Neuroscience Research 15:323–339 (1986).
Alfred W. Sandrock, Jr. and William D. Matthew, Identification of a peripheral nerve neurite growth-promoting activity by development and use of an in vitro bioassay, Proc. Natl. Acad. Sci. USA 84:6934–6938 (1987).
David Edgar et al., Structural Requirements for the Stimulation of Neurite Outgrowth by Two Variants of Laminin and Their Inhibition by Antibodies, The Journal of Cell Biology 106:1299–1306 (1988).
Cornbrooks et al., "In vivo and in vitro observations on laminin production by Schwann cells", Proc. Natl. Acad. Sci. USA vol. 80:3850–3854 (1983).
Engvall et al., "Merosin is a tissue-restricted basement membrane component and a member of a family of laminin like protein", J. Cell Biol., 109 4 part 2, 1989 (New York US), Twenty-Ninth Annual Meeting of the American Society for Cell Biology, Houston, Texas, 5–9 Nov. 1989, Minisymposium 1, Abstract 3.
Ehrig et al., "Merosin, a tissue-specific basement mem-
(List continued on next page.)

*Primary Examiner*—Howard E. Schain
*Assistant Examiner*—P. Lynn Touzeau
*Attorney, Agent, or Firm*—Campbell and Flores

[57] ABSTRACT

A substantially pure heterotrimeric laminin variant comprising the structure M-X-B2, wherein M is the M polypeptide of merosin; X is selected from the group consisting of the B1 chain of laminin and S-laminin; and B2 is the B2 chain of laminin.

7 Claims, 11 Drawing Sheets

PUBLICATIONS brane protein, is a laminin-like protein", Proc. Natl. Acad. Sci. USA vol. 87:3264–3268 (1990).

Hagg et al., "Merosin is associated with neurons of the adult mammalian central nervous system", J. Cell. Biol., 111, 5 part 2, (New York, US), Abstract 2227 (1990).

Engvall et al., "Distribution of four laminin variants: tissues restricted distribution of heterotrimers assembled from five different subunits", Chemical Abstracts vol. 114, No. 9 Abstract 79032r (1991), & Cell Regul. 1(10):731–40 (1990).

Martin, G. R., et al., "Laminin and Other Basement Membrane Components", Ann. Rev. Cell Biol. 3:57–85 (1987).

Lander, A. D., et al., "Laminin is Associated with the 'Neurite Outgrowth-promoting Factors' Found in Conditioned Media", Proc. Natl. Acad. Sci. USA 82:2183–87 (1985).

Davis, G. E., et al., "Isolation and Characterization of Rat Schwannoma Neurite-promoting Factor: Evidence that the Factor Contains Laminin", J. Neurosci. 5:2662–71 (1985).

Steele, J. G., et al., "Neurite-Promoting Activity From Fetal Skeletal Muscle: Partial Purification of a High-–Molecular–Weight Form", J. Neurosci. Res. 15:323–39 (1986).

Sandrock, A. W., et al. "Identification of a Peripheral Nerve Neurite Growth-promoting Activity by Development and Use of an In Vitro Bioassay", Proc. Natl. Acad. Sci. USA 84:6934–38 (1987).

Hassell, J. R., et al., "Isolation of Two Forms of Basement Membrane Proteoglycans", J. Biol. Chem. 260:8098–8105 (1984).

Ohno, M., et al. "Isolation of Laminin From Human Placental Membranes: Amnion, Chorion, and Chorionic Microvessels", Chemical Abstracts, vol. 98, No. 25, Jun. 20, 1983, p. 365, abstract 213310m.

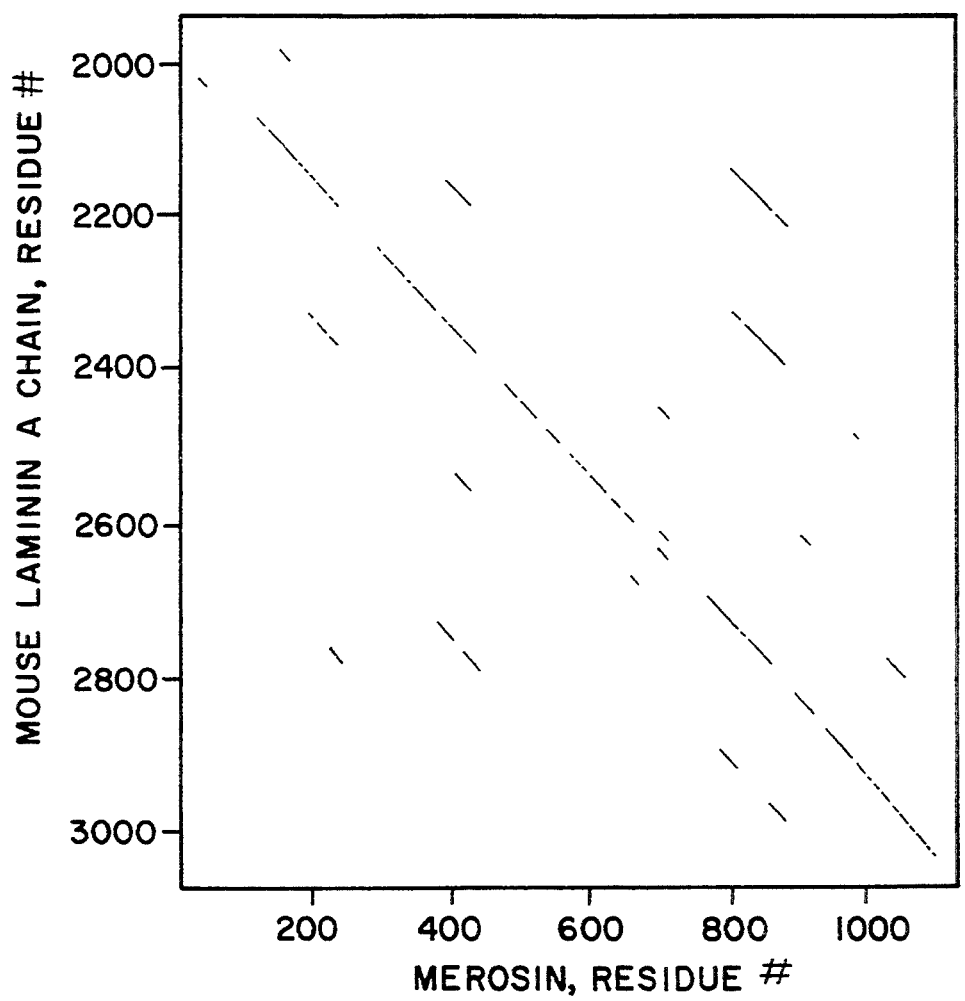

1 2 3 4 5 6 7 8 a-A

TONGUE a-M

TONGUE a-A

HEART a-M

HEART a-A

UMBILICAL CORD a-M

UMBILICAL CORD a-A

TOE a-M

TOE a-A

FETAL MEMBRANES a-M

FETAL MEMBRANES

MEROSIN, NUCLEIC ACIDS ENCODING, FRAGMENTS AND USES THEREOF

The present invention was supported by grants DK 30051, CA 45546, CA 28896 Cancer Center Support Grant CA30199 and R01-NS19195 from the National Institute of Health. The United States Government may have rights in the invention.

This application is a continuation of application Ser. No. 07/587,689, filed Sep. 24, 1990, now abandoned, which is a Continuation-In-Part of U.S. Ser. No. 472,319 filed on Jan. 30, 1990, now abandoned.

BACKGROUND OF THE INVENTION

This invention relates generally to basement membranes and specifically to a novel tissue-specific basement membrane-associated protein.

Basement membranes are thin sheets of extracellular matrix separating epithelial cells from underlying tissue stroma. They compartmentalize epithelial and endothelial organs and maintain tissue structures. In some tissues the basement membrane is a product of the interaction of several cell types; for example, in skeletal muscle, fibroblasts from the endomysium may contribute type IV collagen to the assembly of the basement membrane. The formation of the neural basal lamina requires the interaction of Schwann cells and neurons. Further, basement membranes function in development and tissue repair by promoting attachment, migration and proliferation of cells and by mediating signals for tissue interactions.

All basement membranes contain laminin, type IV collagen, entactin and heparan sulfate proteoglycan. Laminin is a large glycoprotein composed of three polypeptide chains, a 400 kD A chain and two B chains of about 200 kD. The amino-terminal two thirds of the A chain is homologous to the B1 and B2 chains while the carboxy-terminal third has a distinct structure. Laminin promotes attachment, spreading, motility and growth of a variety of cell types. One of the most striking features of laminin is its capacity to promote outgrowth of neurites from cultured neuronal cells. A major site of cell adhesion and the neurite-promoting activity appear to reside in the globular domain at the end of the long arm of this molecule.

The metastatic propensity of certain tumor cells may also be influenced by laminin. For example, laminin has been shown to mediate the attachment of malignant carcinoma cells to type IV collagen and to increase the metastatic potential of murine melanoma cells. Other basement membrane proteins and their receptors may be involved in the adhesion of metastasizing tumor cells to basement membranes of blood vessels and other epithelial tissues.

In addition to the laminin composed of the A, B1 and B2 chains, there are at least two other laminin-related proteins, merosin and S-laminin. The Leivo and Engvall reference, Proc. Natl. Acad. Sci. USA, 85:1544-1548 (1988), incorporated by reference herein, recently described the isolation of a 65-kDa and an 80-kDa precursor, basement membrane-associated protein which was termed merosin. However, there was no disclosure of the approximately 800 kDa protein described herein. Since these 65-kDa and 80-kDa proteins appear to be subunits of the 800 kDa protein, the term "merosin" has now also been applied to the 800 kDa protein described herein.

The other characterized laminin-related polypeptide is S-laminin. The amino acid sequence of this laminin-related polypeptide is most closely related to the B1 chain among the laminin polypeptides (Hunter et al., Nature 338:229-234 (1989), which is incorporated herein by reference). Additionally, other laminin-related polypeptides have been described but not yet structurally characterized, Davis et al., J. Neurosci. 5:2662-2671 (1985); Lander et al., Proc. Natl. Acad. Sci. USA 82:2183-2187 (1985); Aratani, Y. and Kitagawa, Y, J. Biol. Chem. 263:16163-16169 (1988), and Edgar et al., J. Cell Biol. 106:1299-1306 (1988), all of which are incorporated herein by reference.

Immunohistochemical studies led to the belief that laminin is present in all basement membranes throughout development. However, merosin has now been determined to be a muscle- and nerve-specific laminin-like basement membrane protein. This finding, in conjunction with the identification of S-laminin, raises the question of the identity of laminin-like molecules in various basement membranes. These findings also raise the question of whether there exists novel heterotrimeric variants of laminin-related polypeptides.

Because of the critical role of basement membranes in development, tissue repair, neurite growth and cancer, there exists a need for the identification of new basement membrane components as well as a need to identify the heterotrimeric associations of all laminin-related polypeptides and their tissue distributions so as to permit manipulation of these processes. The present invention satisfies this need.

SUMMARY OF THE INVENTION

A substantially pure heterotrimeric laminin variant comprising the structure M-X-B2, wherein M is the M polypeptide of merosin; X is selected from the group consisting of the B1 chain of laminin and S-laminin; and B2 is the B2 chain of laminin.

BRIEF DESCRIPTION OF DRAWINGS

FIGS. 1A, 1B and 1C show the partial DNA sequence of merosin cDNA and the deduced amino acid sequence. Potential N-glycosylation sites are indicated by (▲) and cysteines are circled. Sequences obtained by amino acid sequencing are underlined. Conserved motifs of amino acid sequence are boxed.

FIG. 2 shows a comparison of the amino acid sequences of merosin and the COOH-terminal portion of the mouse laminin A chain by dot matrix plotting. Sequences were compared using the Micro Genie matrix comparison program. The frame was set at eight amino acids with a minimal match of 40%.

FIG. 4 shows an analysis of intact merosin from placenta.

FIG. 6 is an indirect immunofluorescence analysis on tissue sections using monoclonal antibodies to the laminin A chain (antibody 4C7; left panels) or the merosin M chain (antibody 5H2; right panels).

FIG. 7 is an immunofluorescence analysis of laminin and merosin in the myotendinous junction. Sections of toe muscle from 1½ year old infant were stained with monoclonal antibodies in indirect immunofluorescence.

FIG. 8 shows an immunofluorescent analysis of laminin and merosin subunits in placenta. Sections of term placental villi were stained with monoclonal antibodies in indirect immunofluorescence.

DETAILED DESCRIPTION OF THE INVENTION

Figure 1A:
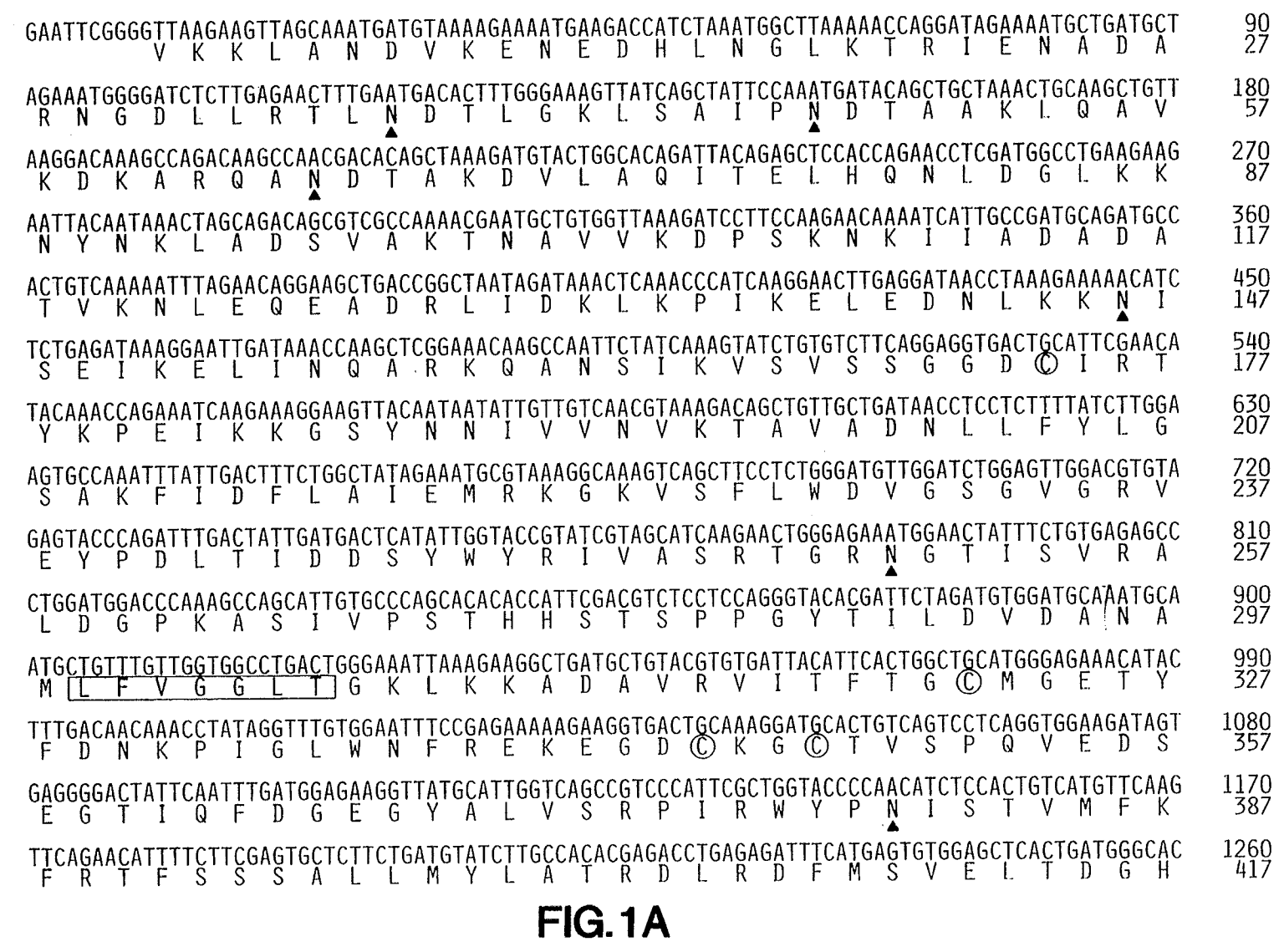
Figure 3A:
FIG. 3 shows immunoblotting of placental extract with peptide antiserum. NaDodSO$_4$ extract of placenta (lanes 1) and the purified fragment of merosin from a pepsin digest of placenta (lanes 2) were electrophoresed on a 2–16% gradient acrylamide gel in the presence of NaDodSO$_4$ and transferred to nitrocellulose. The blot in FIG. 3A was stained with a peptide antiserum raised to a 13-amino acid peptide corresponding to residues 475–488 in FIG. 1. The blot in FIG. 3B was stained with monoclonal antibody that recognizes COOH-terminal fragments of merosin. For comparison, a blot of mouse laminin was stained with anti-laminin as shown in FIG. 3C. Arrowhead shows the position of the top of the separating gel and numbers (kDa) indicated the positions of molecular weight markers.

This invention provides a novel protein, designated merosin, which is structurally related to laminin. The protein has an apparent molecular weight of about 800 kDa and is composed of four polypeptides having apparent molecular weights of 300, 200, 200 and 80 kDa, the 300 kDa polypeptide being joined to the 200 kDa polypeptides by disulfide bonds and the 300 kDa and 80 kDa polypeptides having substantially the amino acid sequence shown in FIG. 1. Merosin is found in placenta, striated muscle, peripheral nerve, trophoblasts and human Schwann cell neoplasms.

This invention also provides novel heterotrimeric variants of laminin and methods of isolating such variants. The novel heterotrimeric variants are composed of a M chain polypeptide in conjunction with either a B1 polypeptide or S-laminin and a B2 chain polypeptide. Such variants exhibit distinct, and at times mutually exclusive, tissue distributions. Each of the variants can be isolated from tissues and used for the study of cell adhesion processes.

It is understood that limited modifications may be made without destroying the biological function of merosin or of any of the subunits of a laminin heterotrimeric variant, and that only a portion of the entire primary structure may be required in order to effect activity. For example, the merosin protein of the invention has an amino acid sequence substantially similar to that shown in FIG. 1, but minor modifications of this sequence which do not destroy its activity also fall within the definition of merosin and within the definition of the protein claimed as such. Moreover, fragments of the sequence of FIG. 1 or of any of the subunits of the variants, but not including the previously described 80 kD fragment which retain the function of the entire protein are included within the definition. It is understood that minor modifications of primary amino acid sequence may result in proteins which have substantially equivalent or enhanced function as compared to the sequence set forth in FIG. 1 or as defined for the heterotrimeric variants. These modifications may be deliberate, as through site-directed mutagenesis, or may be accidental such as through mutation in hosts which are merosin producers. All of these modifications are included as long as merosin biological function is retained. Further, various molecules can be attached to merosin, for example, other proteins, carbohydrates, or lipids. Such modifications are included within the definition of merosin and within the definition of heterotrimeric variants.

"Purified" when used to describe the state of merosin, denotes the protein free of a portion of the other proteins and molecules normally associated with or occurring with merosin in its native environment.

The term "substantially pure," when used herein to describe the state of heterotrimeric laminin variants refers to a level of purity substantially equivalent to that obtained by the experimental procedure described in [Example IV]. This example shows a level of purity which is substantially free of non-laminin family member proteins or other materials normally associated with these proteins in its natural environment. Specific heterotrimeric variants are also substan&lly free from other variants when referred to herein. For example, the substantially pure heterotrimeric variant M-S-B2 means substantially free of naturally associated non-laminin member proteins as well as the laminin family members M-B1-B2, A-B1-B2 and A-S-B2.

As used herein, the term "heterotrimeric laminin variant" refers to a heterotrimeric structure composed of laminin related polypeptides and contains either the laminin A chain polypeptide or the merosin M chain polypeptide in combination with laminin B2 and S-laminin. Functional fragments of any of the polypeptide chains are included as well as functional fragments of the heterotrimeric variant.

Figure 1B:
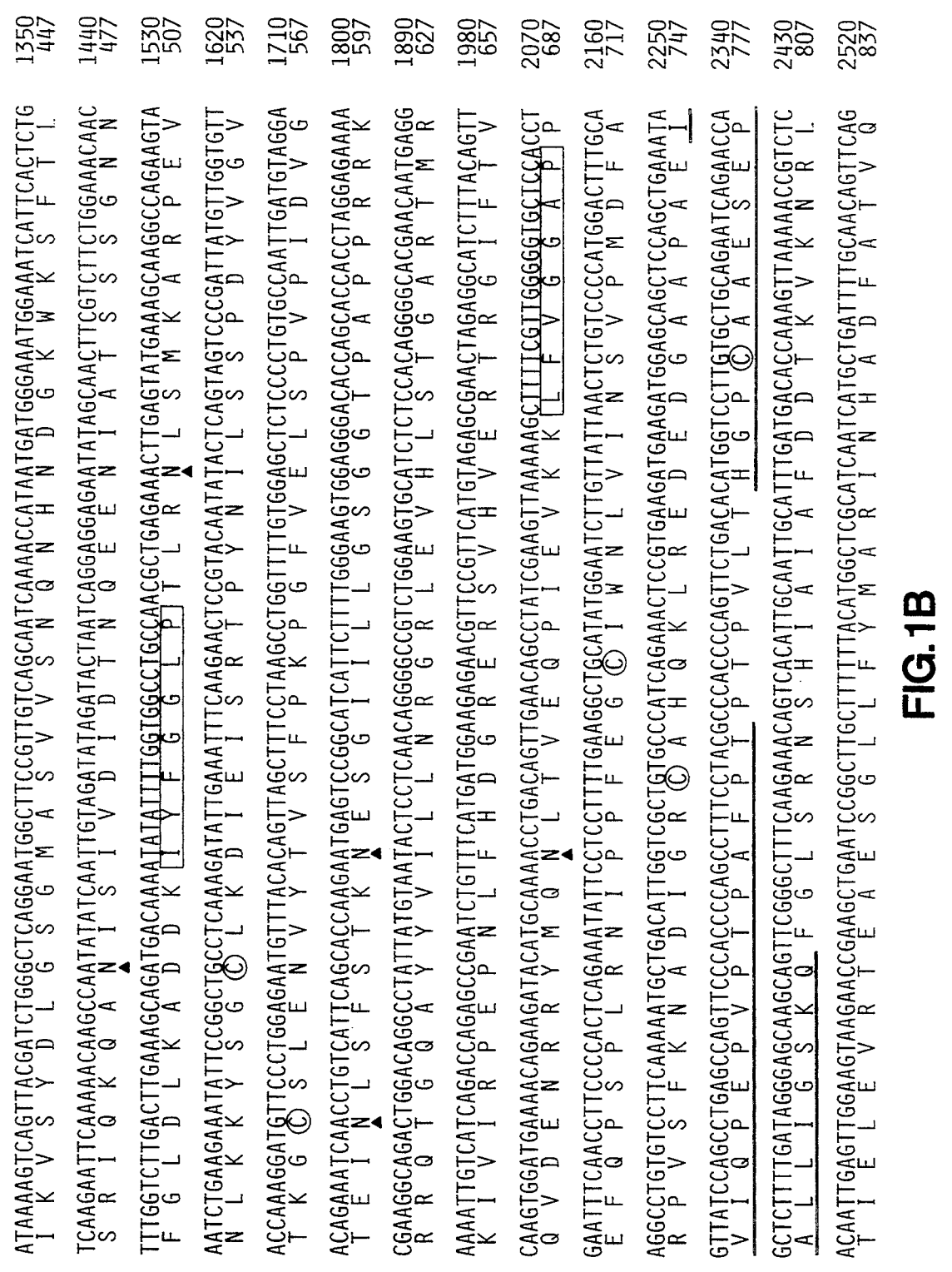

As used herein, the term "merosin M chain" or "M chain polypeptide" refers to a polypeptide substantially equivalent to the large 380 kD subunit of merosin as described in FIG. 1.

As used herein, the term "S-laminin" or "S chain" refers to the 190 kD laminin-related polypeptide as described in Hunter et al., Nature, 338:229-234 (1989), which is incorporated herein by reference.

As used herein, the term "laminin B2" or "B2 chain polypeptide" refers to the 200 kD subunit of laminin as described in Pikkarainen et al., J. Biol. Chem. 263:6751, (1988), which is incorporated herein by reference.

As used herein, the term "laminin Bi" or "B1 chain polypeptide" refers to the 200 kD subunit of laminin as described in Pikkarainen et al., J. Biol. Chem. 262:10454-10462 (1987), which is incorporated herein by reference.

As used herein, the term "selective immunoreactivity" refers to an antibody or antibody fragment which does not cross react, or can be made to not cross react with laminin related polypeptides other than the polypeptide to which the antibody has selective immunoreactivity. Selective immunoreactivity therefore includes binding specificity, affinity and avidity.

"Isolated" when used to describe the state of the nucleic acids encoding merosin, denotes the nucleic acids free of at least a portion of the molecules associated with or occurring with nucleic acids in the native environment.

"Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Host-vector system" refers to cells which have been transfected with vectors constructed using recombinant DNA techniques. The vectors and methods disclosed herein are suitable for use in host cells over a wide range of prokaryotic and eukaryotic organisms.

Reference is made to standard textbooks of molecular biology that contain definitions and methods and means for carrying out basic techniques, encompassed by the present invention. See, for example, Maniatis et al., *Molecular Cloning: A Laboratory Manual*, Cold Spring Harbor Laboratory, New York (1982) and the various references cited therein. This reference and the cited publications are hereby expressly incorporated herein by reference.

In addition, recombinant DNA methods currently used by those skilled in the art include the polymerase chain reaction (PCR) which, combined with the synthesis of oligonucleotides, allows easy reproduction of DNA sequences. A DNA segment of up to approximately 6000 base pairs in length may be amplified exponentially starting from as little as a single gene copy by means of PCR. In this technique a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202 all of which are incorporated by reference herein.

With regard to the present invention, the cDNA shown in FIG. 1 or any portion of it can be reproduced for cloning and expression purposes by amplifying the desired sequence with PCR and cloning it into a suitable vector as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art.

Monoclonal and polyclonal antibodies against merosin were prepared according to procedures well known in the art. The specificity of the antibodies is examined by carrying out enzyme immunoassays and immunoblotting of placental extracts.

Monoclonal antibodies are prepared by immunizing an animal with material containing the protein, such as an extract of human placenta tissue, followed by isolating antibody-producing hybridoma cells, as is well known in the art. (See, for example, Harlow and Lane, ANTIBODIES: A LABORATORY MANUAL, Cold Spring Harbor, 1988, and the references cited therein, all which are incorporated herein by reference.) Antimerosin antibodies are selected by performing immunofluorescence analysis of tissue sections where merosin is localized in the basement membranes of trophoblasts, striated muscle and Schwann cells, but not the membranes of most other tissues. The identification of antibodies is confirmed by immunoblotting and immunoprecipitation which reveals one or more of the polypeptides described above. The appropriate hybridoma is reactive with purified merosin or merosin fragments. Merosin fragments can be prepared by expressing the merosin cDNA shown in FIG. 1 in a prokaryotic or eukaryotic expression vector as described above.

Alternatively, antimerosin antibodies can be prepared by immunizing an animal with synthetic peptides or recombinant protein fragments prepared from the sequence shown in FIG. 1 as is well known in the art. One sequence demonstrated to be suitable for antibody production comprises amino acid residues shown in FIG. 1. Selection of anti-merosin antibodies is performed as described above.

The COOH-terminal portion of merosin is structurally related to the COOH-terminus of the laminin A-chain. However, the amino acid sequence of merosin is 61% and 62% different from the homologous portions of mouse and human laminin A chains, respectively. Affinity purified antibodies stain two bands, suggesting that the merosin polypeptide is processed into two fragments of 300 kD and 80 kD respectively.

cDNA clones for merosin M chain were isolated from a human placental lambda gt11 cDNA expression library using affinity purified antibodies specific for merosin. Two cDNA clones, designated 271 and 225, with inserts of 3.6 and 1.7 kb respectively were selected for sequencing. The nucleic acid sequence of the cDNA revealed a 3.4 kb open reading frame followed by a 155 bp untranslated 3' region. The cDNA and deduced amino acid sequences are shown in FIG. 1. $NH_2$-terminal amino acid sequences of the fragments isolated from peptic or chymotryptic digests of placenta, and the $NH_2$-terminal amino acid sequences of a 16 kD fragment generated with thrombin (Table I) were contained within the deduced sequence, thus defining the clones as merosin cDNA. RNA blot analysis revealed a single transcript of about 10 kb in human placental RNA.

The deduced partial sequence of merosin comprises 1130 amino acids and contains 13 potential sites of N-glycosylation. The sequence includes five repeats of about 190 amino acids. These repeats contain a conserved seven amino acid long sequence, LFVGGLP or variations thereof. This is followed 17-21 and 40-43 residues later by cysteines most of which are preceded by glycines. The average identity among the five repeats is about 25%.

Comparative analysis of the amino acid sequence of merosin with known proteins revealed a striking similarity to the mouse and human laminin A chains. No other significant similarities were found upon search of the data banks. The five repeats of merosin are also present in the COOH-terminal portion of the laminin A chain. The overall identity between the merosin sequence and the corresponding portion of the mouse laminin A chain is 39%.

It has further been discovered that malignant tumors have an insubstantial amount of merosin compared to non-malignant tumors. The precise amount of merosin depends on the specific tumor and can be determined by one skilled in the art given the teaching of this invention.

The invention provides for a substantially pure heterotrimeric laminin variant which consists of the structure M-X-B2, wherein M is the M polypeptide of merosin, X is either the B1 chain of laminin or S-laminin, and B2 is the laminin B2 chain.

The invention provides for a method of isolating a substantially pure M-S-B2 heterotrimeric variant from a M-S-B2 heterotrimeric variant containing material comprising the steps of: a) immobilizing an antibody with selective immunoreactivity to B1 to a solid support; (b) contacting the M-S-B2 containing material with the immobilized antibody with immunoreactivity to B1; c) recovering material unbound to the immobilized antibody with immunoreactivity to B1, wherein the recovered material is a mixture comprising M-S-B2 and A-S-B2; (d) immobilizing an antibody with selective immunoreactivity to M to a solid support; (e) contacting the mixture to the immobilized antibody with immunoreactivity to M; and (f) recovering material bound to the immobilized antibody with immunoreactivity to M, wherein the recovered material is substantially purified M-S-B2. The invention also provides for a method of isolating a M-S-B2 variant where the variant is recovered from an immobilized antibody immunoreactive with S.

Of the previously known laminin heterotrimer and the merosin heterotrimer disclosed herein, either the A chain or the M chain is associated with two B chains. In these heterotrimers, the M chain of merosin is homologous to the laminin A chain. The two polypeptides also have similar sizes. Most basement membranes show a reciprocal expression of laminin and merosin and, therefore, contain either the A chain or the M chain-containing heterotrimers, but not both. One exception is the trophoblast basement membrane which contains both of these polypeptides. This basement membrane may be contributed to by several cell types such as the trophoblast, the syncytiotrophoblast and the intermediate trophoblast cells. Another exception is synaptic basal lamina in muscle and myoteninous and myodermal junctions which may also receive contributions from several cell types and contains both A and M subunits.

The reciprocal expression of the A and M chains in tissues other than the trophoblast basement membrane and the synaptic basal lamina indicates that the heterotrimers characterized by the presence of these subunits are functional alternates for one another in basement membranes. Alternatively, the two proteins are likely to have different functions, despite the apparent similarity of their activities.

The S chain is most closely homologous to the B1 chain of laminin and merosin. As was the case for the A and M chains, the tissue distributions of the S and B1 chains is also reciprocal; most basement membranes contain predominantly one or the other. The B2 chain is found in all basement membranes examined, indicating that homologues of this subunit may not exist. An alternative interpretation is that the antibody used to detect the B2 chain may recognize a conserved region of other, B2-like subunits.

The tissue distribution of the S chain corresponded to that of the A chain rather than the M chain in most tissues. This distribution indicates that the S chain is preferentially included in heterotrimers with the A chain. However, one exception was found in the myotendinous junction. M and S chains co-localized, indicating that heterotrimeric variants containing both the S and M chains can also exist.

A total of four heterotrimers were identified by analysis of isolated heterotrimers from placenta. The polypeptide compositions corresponded to heterotrimers composed of A-B1-B2 chains, which is the classical laminin; M-B1-B2 chains, which is the original merosin; and two heterotrimeric variant-containing S chain polypeptides. The two heterotrimeric variant forms have the structure A-S-B2 and M-S-B2.

The availability of these heterotrimeric variants and antibodies against them will allow analysis of their functional properties. A number of integrins and other molecules are known that are thought to mediate cell adhesion to laminin. Perhaps some of these laminin adhesion molecules might be specific for individual members of the laminin family or to the variants described herein.

The following examples are intended to illustrate but not to limit the invention.

EXAMPLE I

Purification of Merosin

Screening of cDNA Library

A human placental cDNA library in lambda gtll was screened using affinity purified antibodies to denatured 65 kD chymotrypsin fragment of merosin (Table I) as described in Leivo and Engvall, supra. The identity of the isolated cDNA clones was confirmed immunologically following the procedure described by Argraves et al., J. Cell Biol. 105, 1183–1190 (1987) which is incorporated herein by reference.

Determination and Analysis of cDNA Sequences cDNA inserts were cleaved with various restriction enzymes, and fragments subcloned into either M13mp19(+) (Bethesda Research Laboratories, Gaithersburg, MD) or Bluescript SK M13(+) (Stratagene Cloning Systems, La Jolla, Calif.). Nucleic acid sequencing was done by the dideoxy chain termination method of Sanger et al. using deoxyadenosine 5'-α-[$^{35}$S]thiophosphate (New England Nuclear, Boston, Mass.) and a kit from USB (Cleveland, Ohio). Some areas were sequenced using 15-base oligonucleotide primers synthesized using a DNA synthesizer (Applied Biosystems, Foster City, Calif.). Sequence analysis was done using the MicroGenie program (Beckman). Homology searches were carried out using Bionet with EMBL, Genbank, NBRF/PIR and Swiss-Prot databases.

Protein Sequencing

A 55 kD merosin fragment was isolated from a pepsin digest of human placenta using monoclonal antibody affinity chromatography as described in Leivo and Engvall, supra. The pepsin fragment of merosin was digested further with thrombin and a 16 kD fragment was selected for sequence analysis. The merosin fragments were electrophoretically separated on a 10 to 20% gradient polyacrylamide gel in the presence of NaDodSO$_4$, blotted onto polyvinylidene difluoride membranes (Millipore, Boston, Mass.) and sequenced on an Applied Biosystems sequenator as described by Matsudaira, J. Biol. Chem. 262 10035–10038 (1987) incorporated by reference herein.

RNA-blot Analysis

The 800 bp EcoR1 fragment from clone 225 was propagated in the Bluescript vector and labeled with [$^{32}$P]dCTP using the oligo labeling kit from Pharmacia LKB (Piscataway, N.J.). The radiolabeled probe was hybridized to a blot containing RNA from human placenta (Clontech, Palo Alto, Calif.).

Synthetic Peptides, Antibody Production, and Immunoblotting

Two 13 amino acid long peptides CNNFGLDLKADDKI and CSIVDIDTNQEENI were synthesized based on amino acid sequences deduced from the cDNA sequence. The cysteine at the NH$_2$-terminus of these peptides was added to facilitate coupling to carrier protein. The peptides were coupled to keyhole limpet hemocyanin using m-maleimidobenzoyl-N-hydroxysuccinimide ester (Pierce Chemical Co., Rockford, Ill.) according to O'Sullivan et al. (Anal. Biochem 100, 100–108 (1979) incorporated by reference herein. The resulting conjugates were emulsified in Freund's complete adjuvant and injected into rabbits. Boosting immunizations of the conjugate in Freund's incomplete adjuvant were provided one and two months later. The dose of each injection was equivalent to 0.6 mg of peptide. Blood was collected 10 days after the third injection. The antisera obtained were tested against the glutaraldehyde-cross linked peptides in ELISA and against NaDodSO$_4$ extracts of tissue and isolated proteins in immunoblotting as described in Leivo and Engvall, supra.

Figure 3B:
Figure 3C:
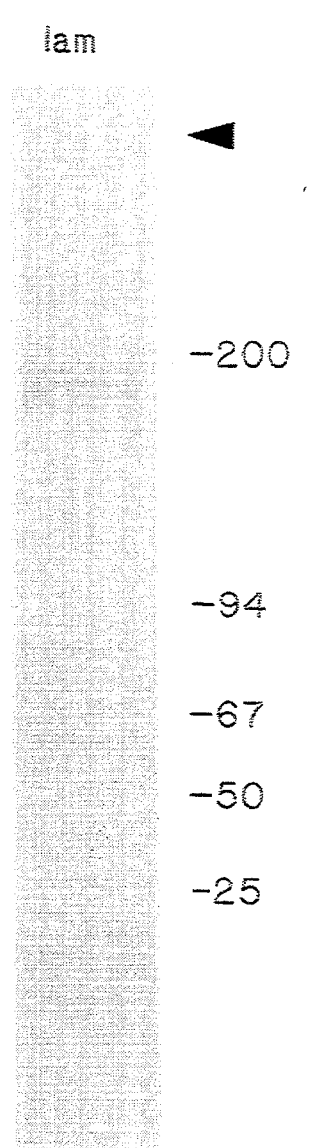

The length of the open reading frame of the merosin cDNA indicated that the mature merosin polypeptide was much larger than the 80 kD fragment identified originally in placental extracts. The deduced amino acid sequence suggested that the 65 kD fragment and the 80 kD tissue polypeptide are COOH-terminal fragments of merosin. The missing portion of the intact merosin polypeptide was identified after synthesizing two 13-amino acid long peptides from the part of the deduced amino acid presumed to be NH$_2$-terminal of the 80 kD fragment (residues 475–488 and 457–469 in FIG. 1). Immunization of rabbits with these peptides resulted in antisera which, in immunoblotting, stained a polypeptide of about 300 kD in NaDodSO$_4$-extracts of placenta. This anti-peptide antisera did not react with the 80 kD or the 65 kD COOH-terminal fragments of merosin. The presence of the 80 kD fragment in the same extract was revealed by a monoclonal antibody (FIG. 3b, lane 1). Antibodies affinity purified from the anti-peptide antiserum on immobilized peptide also stained the 300 kD band. The other peptide antiserum and preimmune sera did not give any staining in immunoblotting. These results suggest that the merosin polypeptide is processed into two fragments of 300 kD and 80 kD, respectively.

Isolation of Intact Merosin from Placenta

Merosin was then isolated using methods previously employed in the isolation of laminin from mouse tissues, Paulsson et al., Eur. J. Biochem, 166:11–19 (1987) incorporated by reference herein. These methods are based on the selective solubilization of laminin from basement membranes with EDTA-containing buffers. When human placenta was sequentially extracted with a neutral buffer and with the same buffer containing EDTA, merosin antigenic activity was found mainly in the EDTA extract. Merosin could be precipitated from the extract with either 4M NaCl or 40% saturated ammonium sulphate. Upon gel filtration on Sepharose 6B, merosin antigenic activity eluted in the void volume peak. It bound to DEAE cellulose and was eluted at about 0.2M NaCl.

Figures 4A, 4B:
FIG. 4A: NaDodSO4-polyacrylamide gel electrophoresis of rat laminin (lane 1) and the merosin-containing fraction from human placenta (lane 2). Positions of molecular weight markers are shown on the left.
FIG. 4B: Electron microscopy after rotary shadowing of the merosin-containing preparation.

FIG. 4 shows NaDodSO$_4$-polyacrylamide gel electrophoresis, electron microscopy after rotary shadowing, and ELISA analysis of the peak merosin-containing fraction from DEAE-cellulose chromatography. The predominant component in this fraction had a molecular weight of about 700 kDa, slightly smaller than the 800 kDa rat laminin, as determined by gel electrophoresis (FIG. 4a). After reduction with mercaptoethanol, the merosin fraction contained polypeptides of about 500 kDa, 300 kDa, and 180–200 kDa in addition to some minor components of 60–90 kDa (FIG. 4a). The synthetic peptide antiserum bound to the 600 kDa and 300 kDa bands in immunoblotting. Antibodies against the COOH-terminal fragment of merosin bound to an 80 kDa band.

Electron microscopy after rotary shadowing was used to further characterize the merosin fraction. Cross-shaped images strongly resembling mouse and rat laminin were the predominant structures seen (FIG. 4b).

Figure 4C:
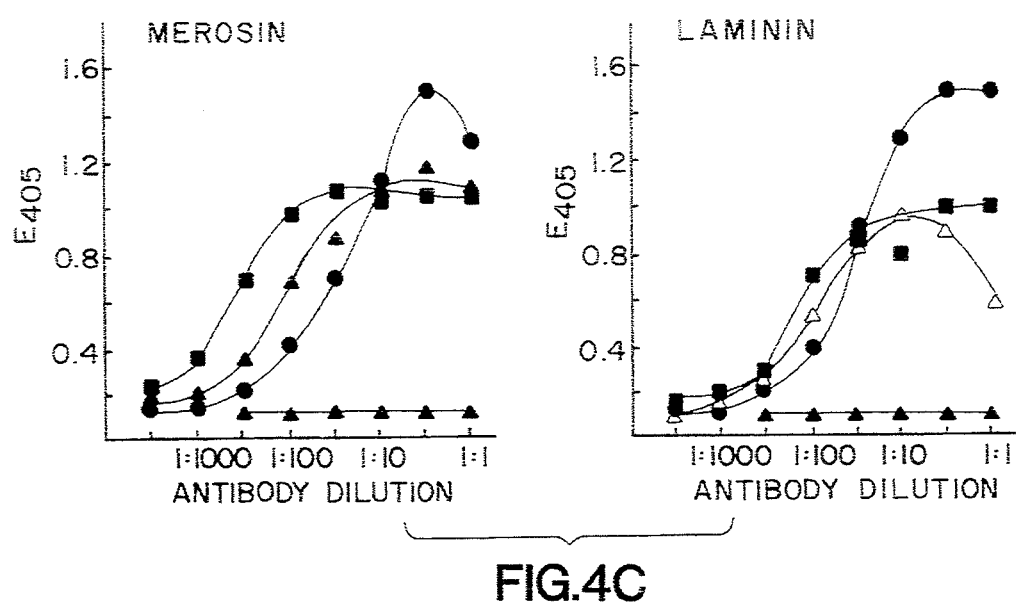
FIG. 4C: ELISA in microtiter wells coated with the merosin-containing preparation and in wells coated with the large pepsin fragment of laminin. The antibodies were 3E5 (■; anti-B1), 2E8 (●); anti-B2), 11D5 (Δ; anti-A), and 2G9 (▲; anti-merosin).

Analysis of the fraction by ELISA with merosin-specific and laminin subunit-specific monoclonal antibodies showed that the preparation contained the merosin polypeptide and the laminin B1 and B2 light chains. No reactivity was obtained with laminin heavy chain-specific antibodies (FIG. 4c). The truncated pepsin fragment of laminin, isolated with laminin heavy chain-specific monoclonal antibody, reacted with antibodies specific for the heavy chain as well as with antibodies specific for the B1 and B2 chains. This laminin preparation did not react with merosin antibodies (FIG. 4c). These results show that the high molecular weight, laminin-like molecule isolated from EDTA-extracts of placenta contained no detectable laminin heavy chain but contained laminin light chains associated with the merosin heavy chain.

EXAMPLE II

Merosin Activity

Merosin Promotes Cell Attachment

Cell attachment promotion by merosin was determined by methods well known in the art and set forth in Engvall and Ruoslahti, Collagen Rel. Res., 3:359–369 (1983) hereby incorporated by reference. Briefly, polystyrene microtiter plates (Flow Laboratories, Irvine, Calif.) were coated with various proteins by incubating the wells with 100 μl of different concentrations of the protein in PBS for 3–16 h at room temperature. Nonbound protein was removed by three washes in PBS. In some experiments, the wells with protein solution were air dried at 37° C. and then washed. Cells were trypsinized and washed twice with 0.5 mg/ml soy bean trypsin inhibitor in EMEM. A suspension of approximately 250,000 cells per ml EMEM with 10mMHEPES was prepared and 0.1 ml was added to each well already containing 0.1 ml EMEM. The plate was then incubated at 37° C. for 30–90 min in an atmosphere of 10% $CO_2$ in air. Cell attachment was evaluated by one or more of the following methods: 1) Nonattached cells were removed and counted; 2) attached cells were fixed, stained with toluidine blue, and counted using an Artek cell counter (Dynatech Corporation, Alexandria, Va.); or 3) the light absorbed by the fixed and stained cells was measured using an automatic ELISA reader (Multiscan, Flow Laboratories). When laminin was tested in solution, it was serially diluted in the plate with a solution of 1 mg/ml BSA in EMEM containing 10 mM HEPES before adding the cells. All assays were done with samples in triplicates.

The cell lines in table 1 have been tested for cell attachment to merosin. Successful attachment is indicated as a "+." The better the attachment the more "+'s."

TABLE 1

| Cell Line | Degree of Attachment | |
|---|---|---|
| | Merosin | Laminin |
| JAR, Chortocarcinoma | + | ++ |
| Endothelial Cells | − | +++ |
| SKLMS, Muscle | ++ | +++ |
| MG63, Osteosarcoma | +++ | +++ |
| U251, Glioma | +++ | +++ |
| IMR 32, Neuroblastoma | +++ | +++ |

The results show that merosin promotes attachment by many but not all types of cells.

Merosin Promotes Neurite Outgrowth

Neurite promoting activity by merosin was determined by known methods as set forth in Engvall et al., J. Cell Biol., 103:2457–2465 (1986) and Manthorpe et al., A Dissection and Tissue Culture, Manual of the Nervous System, 322–326 (1989), Alan R. Liss, Inc., both of which are hereby incorporated by reference. Briefly, embryonic day 8 chick ciliary ganglion neuronal cultures were used. Polyornithine-coated tissue culture plastic wells (6-mm diameter, 96-well microplates) were treated with 5 μg/ml of human laminin or merosin in PBS for 2–3 h at 37° C. The wells were washed once with 100 μl PBS containing 1% BSA. 100 μl culture medium (Dulbecco's modified Eagle's basal medium supplemented with 0.5% BSA, $8 \times 10^{-7}$M insulin, $3.3 \times 10^{-2}$M glucose, $2.6 \times 10^{-2}$M $NaHCO_3$, $2 \times 10^{-3}$M L-glutamine, 100 μm/ml penicillin, and 100 trophic units/ml ciliary neuronotrophic factor) containing 1,000 neurons was added. Cultures were fixed after 3 h by the addition of 200 μl 2% glutaraldehyde for 20 min., washed with water, and stained with 0.1% toluidine blue in water. About 150 neurons were observed microscopically for each culture condition. Neurons were recorded as neurite-bearing if they possessed at least 50 μm of total neurite length.

In addition, surfaces were coated with 100 μg/ml polyoruithine (PORN) for attachment. 25 μg/ml laminin or merosin were then added for neurite outgrowth. Cells were allowed to extend neurites for 72 hours. The degree of promotion is set forth in table 2. Promotion of neurite growth is indicated as a "+." The greater the promotion, the more "+'s."

TABLE 2

| | No Protein | Laminin | Merosin |
|---|---|---|---|
| No Porn | − | − | − |
| Porn | + | +++ | +++ |

The results show merosin is a promotor of neurite outgrowth and, as such, is as efficient as laminin. This suggests that for certain applications (clinical) merosin would be better than laminin for nerve regeneration because it may not have e.g. angiogenic activity.

EXAMPLE III

Merosin Distribution in Human Schwann Cell Neoplasms

Experimental Design

The expression of the basement membrane proteins merosin and laminin was studied immunohistochemically in a series of benign and malignant schwannomas and plexiform neurofibromas. Fresh tissue samples were frozen in liquid nitrogen. Monoclonal antibodies to merosin and laminin were applies to frozen sections, and indirect immunoperoxidase or indirect immunofluorescence techniques were used to detect the two proteins in tissues. The results are described in Leivo et al., Laboratory Investigation, 61:426–432 (1989). This reference and the references cited therein are hereby incorporated by reference.

Methods

Tissue Material

Human neurogenic tumors were obtained fresh without fixation at the Department of Pathology, University of Helsinki. In one instance tissue was derived from the autopsy of a patient with von Recklinghausen's disease who died of a buccal malignant schwannoma. The tissue samples were frozen in liquid nitrogen and embedded in Tissue-Tek OCT (Miles, Naperville, Ill.). The frozen sections were air-dried for 1–2 hours and fixed in acetone. Part of each tissue sample was fixed in formalin and embedded in paraffin for conventional histologic evaluation using hematoxylin-eosin.

Antibodies

Monoclonal antibodies raised to the reduced and alkylated 65-kDa polypeptide fragment of merosin were used. These antibodies detect denatured human merosin, and they blotted an 80-kDa polypeptide band in sodium dodecyl sulfate extracts of human placenta. The following clones of these antibodies given identical staining results were used: 5H2, 4E10, 2G9, 4H2, 1F6, 2E10, and 2D10. Staining results identical to those obtained with monoclonal antibodies have also been obtained in normal tissues with a polyclonal antiserum to merosin. Monoclonal antibodies to nearly intact human laminin have been described, Engvall et al. supra. The monoclonal antibody 2E8 that blots the 200-kDa B1 chain of laminin transferred from sodium dodecyl sulfate-polyacrylamide gels was used.

In immunohistochemical characterization of the Schwann cell tumors, we used a polyclonal rabbit antibody to bovine S-100 protein (Dakopatts, Glostrup, Denmark) at 1:300 dilution and a monoclonal antibody to glial fibrillary acidic protein (Labsystems, Helsinki, Finland) at 1:30 dilution.

Immunohistochemistry

Frozen sections were treated with hybridoma culture medial at 1:2–1:5 dilution. The primary mouse antibodies were applied on sections for 30 minutes or overnight, followed by a 30-minute incubation with biotinylated rabbit antimouse IgG anti-serum (Dako, Copenhagen, Denmark) at 1:500 dilution. Finally, the bound biotin was detected with avidin combined in vitro with biotinylated peroxidase (AB Complex, Dakopatts), both diluted at 1:160. The color was developed with 3-amino-9-ethylcarbazole (Sigma, St. Louis, Mo.) supplemented with 0.02% hydrogen peroxide. In some cases, fluorescein isothiocyanate-coupled goat antimouse IgG (Bio-Rad, Richmond, Calif.) was used to detect bound primary antibodies in indirect immunofluorescence.

For controls of specificity for the staining of merosin, normal mouse serum (1:10) or phosphate-buffered saline were used instead of the hybridoma medium. Controls of specificity for the staining of laminin by monoclonal antibodies have been documented. No significant staining was observed in control experiments. The preparations stained with the immunoperoxidase technique were lightly counterstained with Mayer's hemalum (Merck, Darmstadt, West Germany) to show nuclei. Immunoperoxidase stainings and immunofluorescence preparations were observed and photographed in a Zeiss Axiophot microscope equipped for epi-illumination.

Results

Four human schwannomas, two plexiform neurofibromas, and four malignant schwannomas were examined.

Schwannomas

Two schwannomas were retroperitoneal; one was mediastinal, and one was from the gastric wall exhibiting the histological features of gastric schwannomas. Histologically, all schwannomas showed a relatively uniform spindle cell morphology with focally palisading arrangement of nuclei. Two cases showed an alternating pattern of cellular and loose areas, representing the so-called Antoni A and Antoni B areas, respectively. Electron microscopic examination performed in three cases disclosed spindle cells rich in rough endoplasmic reticulum exhibiting multiple slender cell processes covered by prominent deposition of basement membrane material. These findings were compatible with the ultrastructural features of schwannomas. In immunohistological studies, all schwannomas were strongly positive for S-100 protein. Glial fibrillary acidic protein (GFAP) was focally seen in three cases.

Prominent staining for laminin was seen in parallel layers of basement membranes in the cellular areas and in the entire thickness of the walls of all blood vessels. The loose, less cellular areas of the tumors and the connective tissue sheaths around vessel walls contained no immunoreactive laminin. The cellular areas including the Verocay bodies contained no or only negligible amounts of merosin. However, distinct staining for merosin was regularly seen at the interface where the cellular areas bordered the loose stromal areas or where the cellular areas bordered vascular septa.

Plexiform Neurofibromas

Two plexiform neurofibromas were from nerve trunks of the subcutis of the back and the mediastinum of patients with von Recklinghausen's disease. These tumors represented enlarged tortuous nerve trunks containing wavy collagen and spindle cells compatible with Schwann cells and fibroblasts. In both tumors, merosin and laminin were colocalized in the form of linear immunoreactivity along basement membranes outlining the tortuous nerve fascicles. Laminin was also found in vessel walls. However, no merosin was seen in this location.

Malignant Schwannomas

These tumors originated from deep nerve trunks of femoral, retroperitoneal, and buccal tissues in patients with von Recklinghausen's disease. Histologically they represented malignant high grade spindle cell sarcomas with pronounced mitotic activity and focal areas of necrosis. The malignant schwannomas showed only minimal focal immunostaining for S-100 protein. No staining with antibody to GFAP was detected.

There was only minor focal staining for laminin in some perivascular tumor cells. All vessel walls were, however, strongly positive for laminin. Three of the four malignant schwannomas showed no immunostaining for merosin in the tumor cells. In contrast to laminin, only the external edges of vessel walls showed some staining. In sections where remnants of the original nerve trunks were microscopically identified, staining for merosin outlined the Schwann cell basement membranes of residual normal axons blending into merosin-negative tumor cell areas. A fibrous capsule surrounding malignant schwannomas was negative for merosin. However, in the adjacent striated muscle tissue, the basement membranes were positive for merosin. In one case, small but definite amounts of merosin were seen as punctate deposits between the tumor cells. In this case, a similar pattern of immunostaining for laminin was seen.

Discussion

In brief, the distribution of merosin in schwannomas was more restricted than that of laminin, whereas in plexiform neurofibromas both proteins were present in the same location. No significant amounts of either protein were seen in malignant schwannomas.

In schwannomas, a strong staining for laminin was observed in basement membranes of the cellular Antoni A areas. In contrast, these areas were devoid of merosin. Immunoreactive merosin was seen at the border zone between tumor cells and vessel walls. The discordant distribution of the two basement membrane proteins in schwannomas differs from the situation in normal peripheral nerves where both the merosin and laminin are seen in the Schwann cell basement membranes. The reasons for this difference are unknown, but the result may reflect different biological roles for the two basement membrane proteins. Ultrastructurally, no apparent difference seems to exist between the neoplastic basement membranes of schwannomas and the normal basement membranes surrounding Schwann cells.

The presence of merosin only at the boundaries of the schwannoma cells and nonSchwann cell mesenchymal components demonstrates that the expression of merosin may be induced by a contact or an interaction of schwannoma cells with mesenchymal tissues or extracellular matrices and that no expression occurs by isolated schwannoma cells even in relatively well-differentiated tumors. Analogously, Schwann cells in peripheral nerves may require interactions with other cell types of the nerve fascicles such as the neurons, endoneurial fibroblasts, or perineurial cells for synthesis and/or deposition of merosin. It has been shown that the myelination and assembly of Schwann cell basal lamina in the developing nerve in vitro depend on interactions between the Schwann cell and neuron. Likewise, secretion of type IV collagen by cultured Schwann cells is modulated by a contact with neurons.

In plexiform neurofibromas, large amounts of both merosin and laminin were seen in an identical location. These neoplasms contain increased numbers of Schwann cells and perineurial cells as well as some residual axons contained within an intact perineurial sheath and enlarge the nerve fascicles. Thus, a relatively well-organized tissue architecture presumably essential for the expression of merosin is maintained. The presence of various cell elements within these nerve fascicles allows for many cellular contacts and interactions, and apparently some of these are essential for the secretion of merosin.

In the malignant schwannomas of this study, both merosin and laminin were absent or only minimally expressed. The concomitant lack of immunohistological markers for Schwann cell differentiation such as S-100 protein and GFAP suggests that these tumors are neurogenous sarcomas at a low level of Schwann cell differentiation.

Many cultured human cell lines including schwannomas have been examined for the biosynthesis and secretion of merosin, but the protein has not been found in cell cultures. Conversely, biosynthesis if laminin, type IV collagen, heparan sulfate proteoglycan, and entactin has been repeatedly shown in Schwann cell and schwannoma cell cultures. Moreover, in solid choriocarcinomas merosin was expressed by cells of the intermediate trophoblast type. No merosin could be detected in cultured choriocarcinoma cell lines, although these cell lines synthesized laminin. Apparently, cultured and neoplastic Schwann cells and other cells lose the capacity to secrete merosin but retain some other matrix proteins characteristic of the corresponding mature cells.

During mouse development, significant quantities of merosin were found in muscles and peripheral nerves only after birth. Together with the present results this indicates that the expression of merosin is a feature of mature cells that could be expected only in well-differentiated normal or neoplastic Schwann cells.

EXAMPLE IV

Characterization of Monoclonal Antibodies to the Laminin A Chain

This example shows the generation of monoclonal antibodies specific to the laminin A chain and describes other antibodies specific to laminin-related proteins used in Examples V–VII.

Several monoclonal antibodies against purified pepsin fragments of laminin have been described previously, Engvall et al., J. Cell. Biol. 103:3457–2465 (1986) which is incorporated herein by reference. Three of these antibodies have been shown to recognize the B1 and B2 chains of laminin: antibody 2E8 crossreacts with rat L2 laminin and binds to the smallest of the rat laminin subunits, the B2, in immunoblotting. Two other antibodies, 3E5 and 4E10, which were initially thought to be A chain specific have since been shown to be specific for the B1 chain. (Gehlsen et al. J. Biol. Chem. 264:19034–19038 (1989 which is incorporated herein by reference). Another antibody, 4C7, binds to the globular domain at the end of the long arm. This domain is the C-terminal portion of the A chain and the 4C7 antibody could therefore be against the A chain. However, it has not been previously possible to assign a chain-specificity to this antibody because it does not crossreact with rodent laminin and does not work in immunoblotting. Monoclonal antibodies 5H2 and 2G9 against the C-terminal portion of merosin also have been described, Leivo and Engvall, Proc. Natl. Acad. Sci. USA 85:1544–1548 (1988) which is incorporated herein by reference. Two monoclonal antibodies against S-laminin that crossreact with human laminin, C1 and C4, are also known and have been described by Hunter et al. 1989 supra.

Intact merosin was isolated from placenta as described in Example I. Briefly, one term placenta was rinsed in water and homogenized in 50 mM Tris, pH 7.4, 100 mM NaCl, 0.1 mM PMSF. After centrifugation, the supernatant was discarded. The pellet was extracted overnight in the cold room in 1 liter 10 mM EDTA in Tris-NaCl-PMSF (stirring). After centrifugation, merosin in the supernatant was precipitated by the addition of NaCl to 5M. After 4–24 hours at 10° C., the pellet was collected by centrifugation. The pellet from NaCl precipitation was dissolved in 20 ml 0.5M NaCl, 50 mMTris, pH 7.4, absorbed with 1.5 ml gelatin-Sepharose, and clarified by centrifugation. The supernatant was fractionated on a 10×80 cm column of Sepharose 6B packed and run in 50 mM Tris, 100 mMNaI. Seven ml fractions were collected. The protein eluting in the void volume was collected.

Large pepsin fragments of laminin and merosin were prepared from pepsin digests of term placenta by monoclonal antibody affinity chromatography as described by Wewer et al., J. Biol. Chem. 258:12654–12660 (1983) and Engvall et al., J. Cell Biol. 103:2457–2465 (1986), both of which are incorporated herein by reference, using specific antibodies. Briefly, affinity chromatography on M chain specific antibody was performed by prerunning the placental extracts through plain Sepharose and then through gelatin-Sepharose before applying to the antibody column. The column was washed with PBS and 1M NaCl, and bound material was eluted with 1M acetic acid or 4M KSCN.

A new set of monoclonal antibodies were produced for the purpose of obtaining A chain-specific antibodies. To do so, Balb/c mice were immunized with the pepsin fragments isolated from placenta by an anti-B1 subunit-specific antibody. The immune spleen cells were fused with the myeloma cell line ag8,653 using polyethylene glycol as described by Hessle et al., Differentiation 26:49–54 (1984), which is incorporated herein by reference.

Ten antibodies were found that reacted with the pepsin fragments in immunoblotting. These antibodies were further characterized by immunofluorescence on sections of placenta and fetal membranes. The immunofluorescence were performed on 3 um sections of frozen tissues that were cut on a cryostat and positioned on glass microscope slides. The secions were air dried for 60 minutes. The secions were fixed in ice cold acetone for 10 minutes and then washed in PBS. Each section was covered by about 20 ul of monoclonal antibody, either undiluted medium or ascites diluted 1:100. Incubation with the antibody was done in the cold overnight. The sections were then washed three times in PBS followed by incubation with goat or rabbit anti-mouse IgG labeled with fluorescein for 2 hours at room temperature. The sections were again washed three times with PBS and then examined under a fluorescence microscope.

Two potential M chain antibodies were identified in this test by their staining of the trophoblast basement membrane but not the vascular basement membrane in placental sections. The other 8 antibodies stained both the trophoblast and the vascular basement membranes in placenta. These antibodies were assumed to be against the B1, B2, or A chain.

To determine which of the eight antibodies were B chain specific, the antibodies were analyzed by immunoblotting. Six of the eight antibodies stained either the B1 or B2 chain in merosin. The remaining 2 antibodies, denoted as 1F5 and 11D5, did not stain the B chains or the M chain and were considered to be A chain specific antibodies.

The A chain-specific antibodies, 1F5 and 11D5, were tested for specificity by immunoprecipitation of laminin from JAR cell culture medium. Known B chain antibodies and merosin antibodies were used as controls. The immunoprecipitates were performed from conditioned media of $^{35}$S-labeled cells. The conditioned medium was collected and the following chemicals added, final concentrations in parenthesis: NaCl (0.5M), Tris-HCl, pH 8.0 (50 mM), PMSF (0.1 mM), Triton X-100 (1%), EDTA (10 mM).

Figures 5, 9:
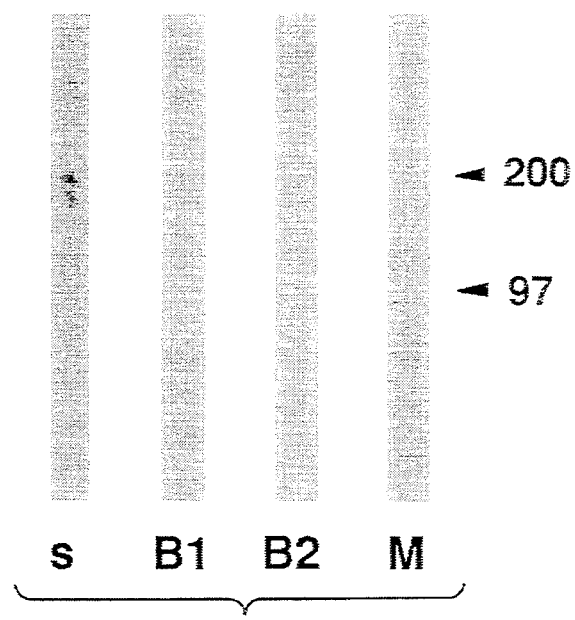
FIG. 5 shows the immunoprecipitation of laminin from conditioned medium of JAR choriocarcinoma cells which were incubated with (35-S)methionine. The antibodies used were: 2E8 anti-B2 (lane 1), 4E10 anti-B1 (lane 2), 4C7 anti-A (lane 3), 2C4 anti-B (lane 4), 1F5 and 11D5 anti-A (lanes 5–6), 1F9 anti-M (lane 7), and control 3E1 (anti-integrin beta 4, lane 8). The 7% acrylamide gel was run under reducing conditions.
FIG. 9 is an immunoblot of isolated intact merosin with antibodies against S (C4), B1 (3E5), B2 (2E8), and the 80 KDa fragment of the merosin M chain (5H2).

To prepare the immunoadsorbent, one ml of a 50% suspension of protein A-Sepharose in PBS with 0.05% Tween 20 was incubated with 1 ml rabbit antiserum to mouse Ig for 60 minutes at room temperature. 50 ul of this mixture was pipetted into individual tubes and the Sepharose beads were washed 1 time with PBS-Tween. 0.5 ml of monoclonal antibody (hybridoma conditioned medium) was added per tube and incubated at room temperature for 2 hours. The beads were washed again with PBS-Tween. Then, 0.5 ml of the labeled medium was added to each tube and incubated 2 hours. After this incubation, the beads were washed 4 times with PBS-Tween and protein bound to the beads was released by boiling the beads in 50 ul SDS-PAGE sample buffer (4% SDS, 0.001M Tris pH 7.5, 20% glycerol). Proteins were fractionated on a 7% acrylamide gel under reducing conditions. The results are shown in FIG. 5. The antibodies that were used, and their specificity, are: (1) 2E8 anti-B2, (2) 4E10 anti-B1, (3) 4C7 anti-A, (4) 2C4 anti-B, (5) 1F5 anti-A, (6) 11D5 anti-A, (7) 1F9 anti-M, and (8) 3E1 anti-integrin B4.

The results show that 1F5 and 11D5 co-precipitated the laminin A chain and its associated B chains. The B chain specific antibodies also co-precipitated all three polypeptides of laminin while the merosin specific antibody did not. Since JAR cells make only the A, B1 and B2 polypeptides, and since 1F5 and 11D5 were not immunoreactive with B1 or B2, these results demonstrated that the co-precipitation of all three laminin polypeptides is through A chain specific interactions. These and other antibodies used herein to localize laminin and merosin subunits are listed in Table I.

TABLE I

Summary of Characteristics of Monoclonal Antibodies

| Antibody | Ig Class | Subunit Specificity | Species Reactivity |
|---|---|---|---|
| 1F5 | IgG1 | A | human |
| 11D5 | IgG1 | A | human |
| 4C7 | IgG2a | A | human rabbit |
| 5H2 | IgG1 | M | human rabbit |
| 2G9 | IgG1 | M | human rabbit |
| 4E10 | IgG1 | B1 | human rabbit |
| 3E5 | IgG1 | B1 | human |
| 2E8 | IgG2a | B2 | human rat |
| C1 | IgG1 | S | human rabbit rat |
| C4 | IgG1 | S | human rabbit rat guinea pig |

EXAMPLE V

Laminin A Chain and Merosin M Chain In Different Basement Membranes

This example shows the differential localization of the laminin A chain polypeptide and the merosin M chain polypeptide.

Figure 6A:
FIGS. 6A and 6B: adult rabbit tongue. ep: epidermis; de: dermis; mu: muscle.
Figure 6B:

The distribution of merosin, as defined by its M chain, and laminin, as defined by its A chain, was assessed by immunofluorescence in the basement membrane of adult skeletal muscle fibers. Merosin is known to be abundant in these fibers; however, the distribution of the A chain in this location has not been determined. Immunofluorescence with the A chain specific antibodies revealed a striking lack of staining in the muscle fiber basement membrane in tongue. (FIG. 6A) The antibodies strongly stained blood vessels in muscle and dermis as well as the epidermal basement membrane. Anti-A chain antibodies 1F5 and 11D5 as well as the previously characterized antibody 4C7 gave the same staining pattern in all human tissues. Antibody 4C7 crossreacts with rabbit basement membranes. This crossreactivity allowed the use of the more readily available rabbit tissues for some experiments. The above results (FIG. 6A and B) demonstrated that the basement membrane of the mature muscle fiber contained predominantly merosin (the M chain associated with B chains) and little or no laminin (the A chain associated with B chains).

Figure 6C:
FIGS. 6C and 6D: adult rabbit heart.
Figure 6D:
Figure 6E:
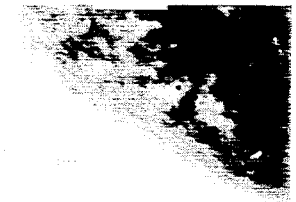
FIGS. 6E and 6F: human umbilical cord. sm: smooth muscle; ct: connective tissue.
Figure 6F:
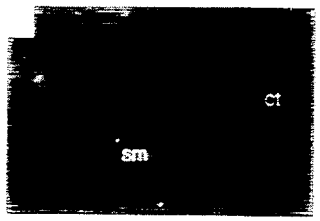
Figure 6G:
FIGS. 6G and 6H: human toe tissue from 1½ year old infant. Arrows point to four different peripheral nerves.
Figure 6H:
Figure 6I:
FIGS. 6I and 6J: human fetal membranes. am: Amnion; ch: Chorion; it: Intermediate trophoblast. Bar=50 um.
Figure 6J:
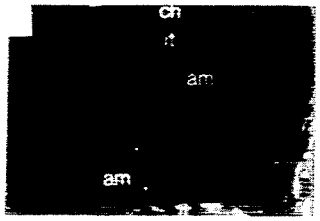
Figure 7A:
FIG. 7A: anti-M (5H2)
Figure 7C:
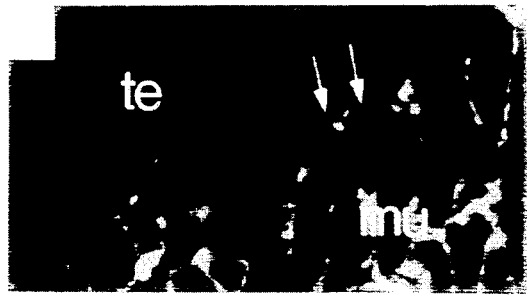
FIG. 7C: anti-B1 (4E10)
Figure 7D:
FIG. 7D: anti-B2 (2E8)
Figure 7B:
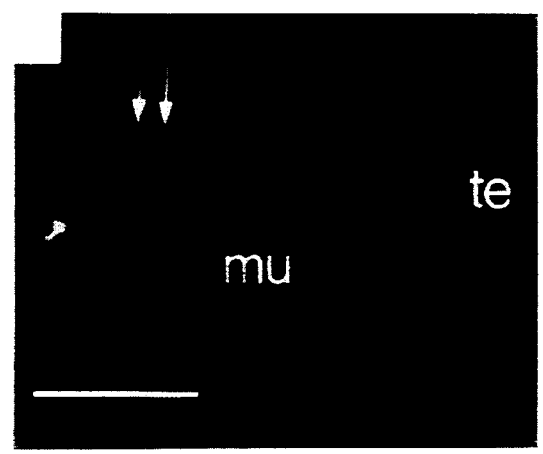
FIG. 7B: anti-A (4C7)
Figure 7E:
FIG. 7E: anti-S (C4) mu: muscle; te: tendon; Double arrows indicate the myotendinous junction. Bar=50 um.
Figure 8C:
FIG. 8C: anti-B2 (2E8)
Figure 8B:
FIG. 8B: anti-B1 (4E10)
Figure 8A:
FIG. 8A: anti-A (4C7)
Figure 8E:
FIG. 8E: anti-S (C4) Bar=50 um.
Figure 8D:
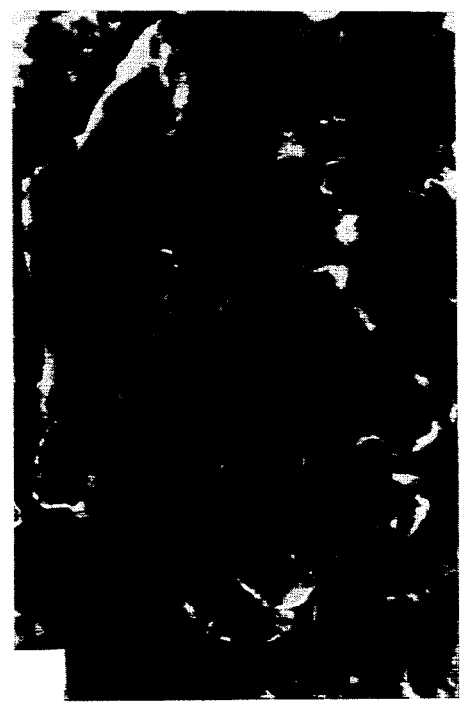
FIG. 8D: anti-M (5H2)

The presence of laminin and merosin in basement membranes other than skeletal muscle was also investigated (FIG. 6C–J). Immunofluorescent results showed that in the heart, laminin A chain was absent from the muscle but present in blood vessels similarly to what was found in skeletal muscle (FIG. 6C). The A chain was, however, present in the smooth muscle of human umbilical cord, monkey colon, and rabbit stomach and bladder whereas the M chain was not detected in these tissues (FIG. 6E and F). In peripheral nerve, A chain staining was abundant in the perineurium, while the M chain was predominantly found in the Schwann cell basement membrane (FIG. 6G and H). In fetal membranes, the A chain was detected in all epithelial basement membranes of the amnion and chorion. The M chain was found only in the layer of the intermediate trophoblast cells (FIG. 6I and J). These results demonstrate that most basement membranes contain either the A chain or the M chain polypeptides, but rarely both.

EXAMPLE VI

The Laminin A Chain and the Merosin M Chain Can Associate With Either the B1 Chain or S-Laminin This example demonstrates the co-localization of the merosin M polypeptide with S-laminin and laminin B2.

The distribution of S-laminin is restricted to synaptic sites in muscle, to the perineurium in peripheral nerve, and to certain blood vessels and the glomeruli in the kidney. These are all basement membranes that contain the A chain but not the M chain. These results indicated that laminin can have the subunit composition A-B1-B2 or A-S-B2, while merosin can only occur as the trimer M-B1-B2. However, the basement membrane of the myotendinous junction was observed to contain M and to lack B1 as determined by immunofluorescence (FIG. 7). The same increased staining pattern observed with M chain antibodies was also seen with a B2 antibody but not with the A chain antibody (FIG. 7). However, antibodies against S-laminin intensely and selectively stained the muscle attachment sites. These results demonstrate that molecules with the composition M-S-B2 are responsible for the staining pattern at the myotendinous junction.

EXAMPLE VII

Isolation of S-Merosin From Placenta

This example shows the isolation of laminin heterotrimeric variants from human placenta.

Placenta is a rich source for both laminin and merosin Wewer et al. 1984, supra; Dixit, S. N., Connect. Tissue Res. 14;31–40 (1985) and Ohno et al., Biochem. Biophys. Res. Commun. 112:1091–1098 (1983), all of which are incorporated herein by reference. The placenta is also rich in vasculature and might contain S-laminin which is found in many blood vessels. To determine whether this tissue contained S-laminin, placental sections were stained with antibodies to the different laminin and merosin polypeptides (FIG. 8). The A, B1, and B2 polypeptides were present in both the trophoblast basement membrane and the basement membrane of the fetal capillaries, while the M polypeptide is present only in the trophoblast basement membrane. The S-laminin antibodies were found to stain predominantly the trophoblast basement membrane.

To determine whether placenta contains merosin with the subunit composition M-S-B2 in addition to merosin with the subunit composition M-B1-B2, small amounts of merosin from EDTA extracts of placenta were isolated by affinity chromatography on an M chain specific antibody. The eluted preparation of merosin was tested for the presence of B1, B2, and S chains by ELISA and by immunoblotting. The results of the immunoblot are shown in FIG. 9. Antibodies against B1, B2, and S all reacted predominantly with 200 kD polypeptides in the merosin preparation. Fainter bands of higher molecular weight may represent cross-linked B chains. The anti-S antibody stained additional bands below the 200 kD region. Since the number and position of these extra bands varied between preparations, it is possible that they represent degradation products. Antibodies against the 300 kD and the 80 kD portions of the M chain reacted with the 300 kD and the 80 kD (FIG. 9) polypeptides, respectively. These results demonstrate that the merosin prepared this way contained the B1 and B2 chain polypeptides and S-laminin. This result indicates that M and B2 can be associated with S-laminin to form a heterotrimeric variant.

Figure 10:
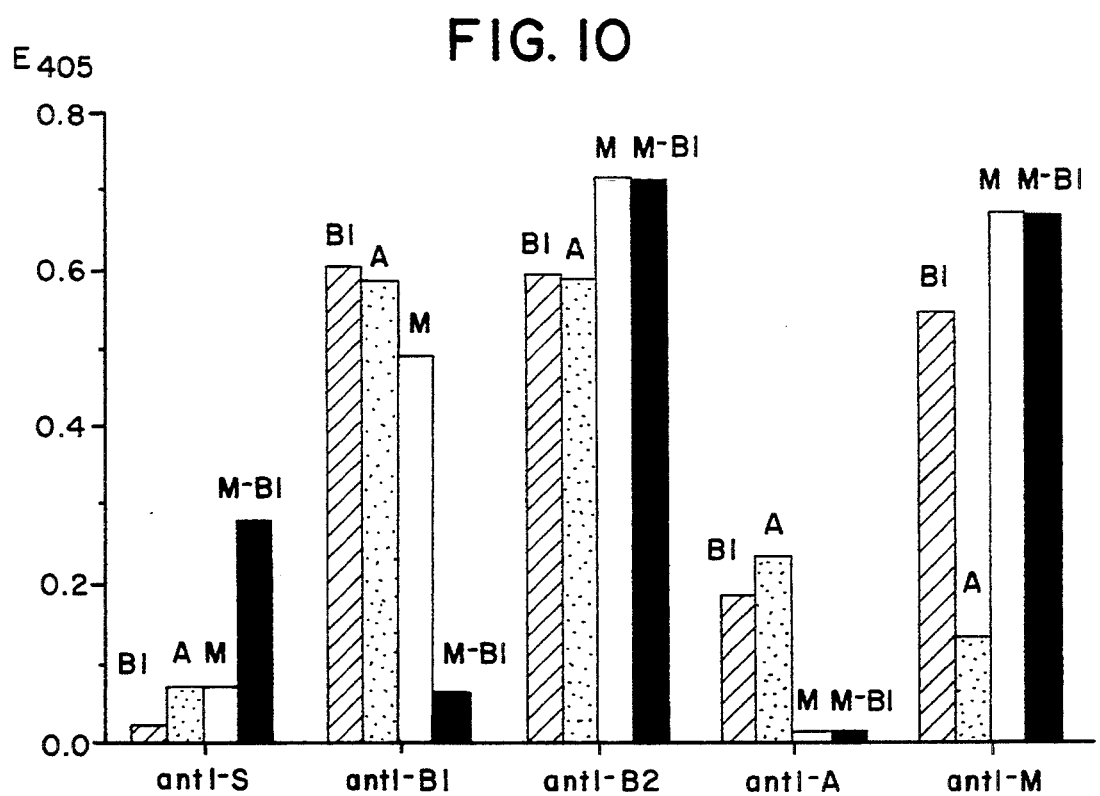
FIG. 10 shows the quantitation of laminin-related polypeptides in affinity purified preparations as measured by ELISA. Heterotrimeric proteins were isolated from a pepsin digest of placenta by affinity chromatography on either 4E10 anti-B1 Sepharose (B1, striped columns), 4C7 anti-A sepharose (A, dotted columns), and 5H2 anti-M Sepharose (M, open columns). Protein was also isolated from a digest, which had been depleted of anti-B1 reactive material, on 5H2 anti-M Sepharose (M-B1, solid columns). Microtiter wells were coated with approximately 1 ug/ml of each preparation. The relative amounts of the different subunits in the preparations were determined after incubation with antibodies C4 (anti-S), 4E10 (anti-B1), 2E8 (anti-B2), 11D5 (anti-A0, and 2G9 (anti-M). Bound antibody was determined after incubation with alkaline phosphatase labeled anti-mouse IgG and measurement of bound enzyme activity (E 405).

Because isolation of intact merosin and laminin by antibody affinity chromatography results in very poor yields, truncated forms of merosin and laminin were isolated from pepsin digests of placenta. Four types of samples were prepared; three were obtained by affinity chromatography on anti-B1, anti-M, and anti-A antibodies, respectively. The fourth preparation was prepared by affinity chromatography on the anti-M antibody of an extract that had been depleted of B1-reactive material by repeated passage through the anti-B1 column. It should be noted that the order of depletion and isolation of variants by affinity chromatography can be reversed and is known to one skilled in the art. Additionally, different antibody columns can be used in different orders than those described here. The order and antibody columns which can be used to isolate all of the heterotrimeric variants is known by one skilled in the art. The above four samples were then tested for the presence of the different laminin and merosin subunits by binding of subunit-specific antibodies in ELISA (FIG. 10).

ELISAs were performed by coating microtiter wells with protein at 1 ug/ml in 0.5 M sodium carbonate by simple adsorption at room temperature overnight. Before assay, the wells were washed with PBS-0.05% Tween 20 twice. Serial dilutions of different antibodies were made in PBS-Tween and 0.1 ml added per well and incubated for 2 hours at 37° C. The wells were washed 3 times with PBS-Tween and then incubated with alkaline phosphatase-labeled anti-mouse IgG, 1:1000 in PBS-Tween, for 2 hours at 37° C. After washing 3 times with PBS-Tween, the enzyme activity bound to the wells was measured. Enzyme substrate buffer: 1 mg/ml p-NPP in 1 M diethanolamine-buffer, pH 9.8, 1 mM MgC12. The color development was measured at 405 nm.

The results showed that S-laminin was not present in the sample that was isolated on an anti-B1 column, independently supporting the above results (i.e., that S can substitute for B1 but is not present in the same molecules as B1). The materials isolated with either the A or the M-specific antibodies contained low but significant levels of S-laminin. The highest level of S-laminin was present in the merosin preparation isolated from a B1 chain-depleted digest. The B1 chain was present in each of the preparations that had not been specifically depleted of B1, while the B2 chain was present at similar levels in all four preparations. The specificity of the isolation procedure was established by the absence of the M chain in the anti-A isolated material and the low amount of the A chain in the anti-M isolated preparation.

Although the invention has been described with reference to the presently-preferred embodiment, it should be understood that various modifications can be made without departing from the spirit of the invention. Accordingly, the invention is limited only by the following claims.

What is claimed is:

1. A substantially pure heterotrimeric laminin variant comprising the structure M-X-B2, wherein M is the M polypeptide of merosin; X is selected from the group consisting of the B1 chain of laminin and S-laminin; and B2 is the B2 chain of laminin.

2. The substantially pure heterotrimeric laminin variant of claim 1 wherein X is S-laminin.

3. The substantially pure heterotrimeric laminin variant of claim 1 wherein X is the B1 chain of laminin.

4. A method of isolating a substantially pure M-S-B2 laminin variant from a M-S-B2 laminin variant containing material comprising M-S-B2 and A-S-B2 laminin variants, comprising the steps of:
   (a) immobilizing an antibody with selective immunoreactivity to B1 to a solid support;
   (b) contacting said M-S-B2 containing material with said immobilized antibody with immunoreactivity to B1;
   (c) recovering material unbound to said immobilized antibody with immunoreactivity to B1, wherein said recovered material is a mixture comprising M-S-B2 and A-S-B2;
   (d) immobilizing an antibody with selective immunoreactivity to M to a solid support;
   (e) contacting said mixture to said immobilized antibody with immunoreactivity to M; and
   (f) recovering material bound to said immobilized antibody with immunoreactivity to M, wherein said recovered material is substantially purified M-S-B2.

5. The method of claim 4 wherein the material not bound to said immobilized antibody with immunoreactivity to M is recovered prior to step (f) and is substantially purified A-S-B2.

6. A method of isolating a M-S-B2 laminin variant from a M-S-B2 laminin variant containing material comprising M-S-B2 and M-B1-B2 laminin variants, comprising the steps of:
   (a) immobilizing an antibody with selective immunoreactivity to M to a solid support;
   (b) contacting said M-S-B2 containing material with said immobilized antibody with immunoreactivity to M;
   (c) recovering material bound to said immobilized antibody with immunoreactivity to M, wherein said recovered material is a mixture comprising M-S-B2 and M-B1-B2;
   (d) immobilizing an antibody with selective immunoreactivity to S to a solid support;
   (e) contacting said mixture to said immobilized antibody with immunoreactivity to S; and
   (f) recovering material bound to said immobilized antibody with immunoreactivity to S, wherein said recovered material is substantially purified M-S-B2.

7. The method of claim 6, wherein the material not bound to said immobilized antibody with immunoreactivity to S is recovered prior to step (f) and is substantially purified M-B1-B2.

* * * * *

UNITED STATES PATENT AND TRADEMARK OFFICE
CERTIFICATE OF CORRECTION

PATENT NO. : 5,444,158
DATED : Aug. 22, 1995
INVENTOR(S) : Engvall and Sanes

It is certified that error appears in the above-indentified patent and that said Letters Patent is hereby corrected as shown below:

On the title page, and column 1, change the title to read--
--Heteromeric Variants of Laminin-Like Proteins--.

In column 5, line 23, please delete "Bi" and replace therefor with --B1--.

In column 11, line 47, please add a space between mM and HEPES.

In column 12, line 68, please delete "applies" and replace therefor with --applied--.

In column 17, line 40, please delete "secions" and replace therefor with --sections--.

In column 18, line 27, please delete "B4" and replace therefor with --β4--.

Signed and Sealed this

Fifth Day of November, 1996

Attest:

BRUCE LEHMAN

Attesting Officer     Commissioner of Patents and Trademarks